United States Patent [19]
Cohen et al.

[11] Patent Number: 5,167,239
[45] Date of Patent: Dec. 1, 1992

[54] ANCHORABLE GUIDEWIRE

[75] Inventors: Donald M. Cohen, Irvine; Alfredo Soria, Garden Grove; Edmund E. Spaeth, Orange; Alan de la Rama, Cerritos, all of Calif.

[73] Assignee: Endomedix Corporation, Irvine, Calif.

[21] Appl. No.: 708,251

[22] Filed: May 30, 1991

[51] Int. Cl.⁵ .............................................. A61B 5/00
[52] U.S. Cl. .................................... 128/772; 128/657; 604/96
[58] Field of Search .............................. 128/657, 772; 604/96-103, 280, 282; 137/537, 538, 540

[56] References Cited

U.S. PATENT DOCUMENTS

| | | | |
|---|---|---|---|
| 3,913,565 | 10/1975 | Kawahara | 128/772 |
| 4,299,226 | 11/1981 | Banka | 128/657 |
| 4,318,410 | 3/1982 | Chin | 604/98 |
| 4,351,341 | 9/1982 | Goldberg et al. | 604/96 |
| 4,387,711 | 6/1983 | Merry | 604/96 |
| 4,682,625 | 7/1987 | Christopher | 137/538 |
| 5,045,061 | 9/1991 | Seifert et al. | 128/772 |
| 5,054,500 | 10/1991 | Littleford et al. | 128/772 |
| 5,059,177 | 10/1991 | Towne et al. | 128/657 |

FOREIGN PATENT DOCUMENTS 2203650  10/1988  United Kingdom ................ 128/772

OTHER PUBLICATIONS

Rizzo, T. F., et al., "Dilating Guide Wire: Use of a New Ultra-Low-Profile Percutaneous Transluminal Coronary Angioplasty System"; *Catheterization and Cardiovascular Diagnosis* 16:258-262 (1989).

Avedissian, M. G., et al., "Percutaneous Transluminal Coronary Angioplasty: A Review of Current Balloon Dilatation Systems"; *Catheterization and Cardiovascular Diagnosis*, 18:263-275 (1989).

den Heijer, P., et al., "Coronary Angioplasty Using the Probing Catheter in Combination with the Probe TM Balloon Wire"; *The American Journal of Cardiology*, 64:1041-1043 (1989).

*Primary Examiner*—Max Hindenburg
*Attorney, Agent, or Firm*—Stetina and Brunda

[57] ABSTRACT

An anchorable guidewire for use in various medical applications, said guidewire comprising an elongate guidewire body with at least one inflatable anchoring member or balloon positioned thereon and a deactuatable check valve operative to maintain inflation of the inflatable anchoring member or balloon until such time as the check valve is volitionally deactuated by a human operator. The inflatable anchoring member or balloon is preferably sized, constructed and configured such that, when fully deflated, the anchoring member or balloon will fully collapse against the outer surface of the guidewire without substantial protrusion or extension therebeyond.

33 Claims, 3 Drawing Sheets

ANCHORABLE GUIDEWIRE

FIELD OF THE INVENTION

The present invention relates generally to medical devices and more particularly to an anchorable guidewire usable for guiding the insertion of catheters, scopes or other instruments into specific ducts, passageways, vessels or cavities of the human body and also usable for retrieving, dislodging or moving solid objects (e.g. stones, foreign bodies, etc., . . . ) which are positioned in ducts, passageways, vessels or cavities of the body.

BACKGROUND OF THE INVENTION

Many medical procedures utilize elongate flexible guidewires for guiding the insertion of catheters, scopes or other instruments into ducts, passageways, vessels or cavities of the body. Typically, such guidewires are formed of continuous coils of thin steel wire tightly wound about a longitudinal steel core, so as to form an elongate continuous wire coil having an outer diameter of approximately 0.021–0.038 in. The outer surface of such elongate wire coil may be covered with a smooth, inert plastic coating such as a fluorocarbon (TEFLON TM) coating.

In many cardiovascular procedures, guidewires are often used to guide the insertion of catheters (e.g. angiographic catheters, balloon dilation catheters, pressure monitoring catheters, . . . ) to specific locations within the vascular anatomy. It is the usual practice, in such cardiovascular applications, to first insert the guidewire into a peripheral blood vessel and to subsequently advance the guidewire, under radiographic guidance, to a point at which the distal portion of the guidewire is positioned at or near a specific lesion or anatomical structure. A selected catheter or instrument (e.g. angiography catheter, balloon dilation catheter, angioscope, . . . ) is then advanced over the pre-positioned guidewire to a position adjacent the desired operative site.

In gastroenterologic procedures, guidewires are often used to guide the advancement of catheters, endoscopic looking devices or other instruments through various portions of the gastrointestinal tract or biliary tree. In many such gastroenterologic procedures, guidewires are initially inserted through a gastroscope or duodenoscope and subsequently advanced, with or without radiographic guidance, to the desired operative location within the gastrointestinal tract or biliary tree. After the guidewire has been so positioned, a selected catheter, endoscope or other instrument (e.g. a stent, bougie or balloon for dilating a stricture) is advanced over the guidewire, to a position at or near the desired operative site.

In other procedures, such as certain laparoscopic surgical procedures, guidewires may also be transabdominally inserted, through appropriate introducers or trochars, and used to guide and position catheters, scopes and/or other instruments.

During any or all of the above described procedures, it is, from time to time, necessary or desirable to extract, remove, reposition or exchange a catheter, scope or other instrument which has already been inserted over a previously positioned guidewire. In such instances, it is highly desirable that the extraction, removal, repositioning or exchange of the catheter, scope or instrument be effected without causing withdrawal, retraction, disruption or significant movement of the pre-positioned guidewire.

In the prior art, the ability to hold a guidewire still while manipulating or exchanging a catheter, scope or other instrument which has been inserted over the guidewire has been largely dependent upon the level of accomplishment and skill of the practitioner who is conducting the procedure. To wit, the practitioner must exercise extreme caution to avoid jerking or pulling of the guidewire while carrying out the desired manipulation or exchange of the attendant catheter, scope or other instrument. In view of the potential for inadvertent movement of the guidewire, despite the best efforts of the practitioner, it is highly desirable to devise an improved guidewire which incorporates an anchoring member for anchoring and holding the guidewire in place within a tube, duct or other anatomical structure during the occasional exchange or manipulation of the attendant catheter, scope or instrument. It is further desirable that such anchoring member be incorporated into the guidewire without substantially increasing the diameter of the guidewire and without otherwise interfering with the normal mode of use of such guidewire.

The prior art has included a device for immobilizing a guidewire during use. Such device is attachable to the extracorporeal (proximal) portion of a previously inserted guidewire for the purpose of fixing or immobilizing the guidewire during or after an operative procedure. Gavant, M. L. IMPROVED GUIDEWIRE IMMOBILIZATION TECHNIQUE FOR INTERVENTIONAL PROCEDURES; American Journal of Radiology 149:629–630 (September 1987). Such device does not serve to anchor the intracorporeally inserted portion of a guidewire to a surrounding or adjacent anatomical structure.

Also, the prior art has included at least two (2) angioplasty guidewires which have inflatable balloon dilation systems mounted thereon (i.e. "balloon-on-a-wire" systems). See, Rizzo, T. F.; Ciccone, J. and Werre, R.; "DILATING GUIDE WIRE: USE OF A NEW ULTRA-LOW PROFILE PERCUTANEOUS TRANSLUMINAL CORONARY ANGIOPLASTY SYSTEM"; *Catheterization and Cardiovascular Diagnosis,* 16:258–262 (1989). The dilation balloons mounted on these prior art balloon-on-a-wire systems are intended for use in effecting angioplastic dilation of stenotic vascular lesions, not for anchoring. Such dilation balloons are not appropriately sized, configured or constructed to optimally carry out an anchoring or holding function. One such prior art "balloon-on-a-wire" system is commercially available under the name USCI PROBE (C. R. Bard, Inc., USCI Division, Billerica, Mass.). The other such balloon-on-a-wire system is commercially available under the name SCI-MED ACE (Sci-Med Systems Inc., Minneapolis, Minn.). Both of these prior art balloon-on-a-wire systems comprise flexible guidewires whereupon relatively large annular dilation balloons are mounted. Such balloons are sized and configured to effect a dilation function in accordance with normal transluminal angioplasty techniques. Such balloons are, however, relatively large and bulky and, even in their deflated states, such balloons substantially alter the outer surface and diameter of the guidewire body. Thus, even when deflated, the presence of such balloon could interfere with passage of the guidewire through tight openings, strictures or the like. Furthermore, because these previous balloon-on-a-wire systems are not intended for use as means for guiding the advancement of a separate catheter, scope or instrument thereover, they do require the continuous and uninterrupted attachment of a bulky hub, stopcock and/or syringe on the proximal end of the guidewire during the entire time in which the balloon is inflated. The presence of such bulky hub, stopcock and syringe on the proximal end of the guidewire essentially precludes the passage of a catheter, scope or other instrument over the proximal end of the guidewire. Furthermore, if the attendant hub, stopcock and/or syringe were to be removed from the proximal end of the guidewire (as would permit advancement/retraction of a catheter thereover), such would result in deflation of the balloon, as the prior art balloon-on-a-wire systems do not incorporate any sort of check valve or other apparatus which would maintain inflation of the balloon even when the hub, stopcock and/or syringe used for inflation of the balloon has been removed from the proximal end of the guidewire.

In view of the state of the prior art, there exists a need for development of a flexible guidewire having an expandable or inflatable anchoring member (e.g. a balloon) disposed on the body thereof to anchor and hold the distal portion of the guidewire in a relatively fixed position while catheters, scopes or other instruments are advanced/retracted over the proximal end and/or body of the guidewire.

SUMMARY OF THE INVENTION

The present invention overcomes some or all of the shortcomings of the prior art by providing an anchorable guidewire having (a) an inflatable anchoring member such as a balloon disposed on the body of the guidewire and (b) a check valve for maintaining inflation of the anchoring member or balloon until such time as the check valve is manually opened to allow deflation of the balloon.

In accordance with the invention, there is provided an anchorable guidewire device comprising (a) an elongate guidewire body having a hollow lumen extending longitudinally at least partially therethrough; (b) an inflatable anchoring member or balloon mounted at a first location on the guidewire body; c) an injection port or fixture at a second location on the guidewire body, proximal to said first location, and on a region of the guidewire which remains exteriorized during standard operation; d) a lumen passageway or other fluidic interconnection between the injection port/fixture and the inflatable member or balloon to permit fluid to be injected through such port or fixture and into said balloon; and (e) a check valve apparatus operatively communicative with the fluidic interconnection between the injection port/fixture and the inflatable anchoring member/balloon to prevent deflation of the anchoring member or balloon until such time as the check valve is manually deactuated by a human operator.

The elongate guidewire body of the device may comprise a straight solid wire or may comprise a coiled wire member, coiled about a longitudinal axis to define a hollow inner bore or lumen extending therethrough. An elongate inner tubular member may be disposed within such inner lumen, such that the coiled wire member is coiled upon the surface of the elongate inner tubular member.

The inflatable anchoring member or balloon may be formed in any size or configuration to facilitate anchoring and holding the guidewire body within any particular duct, vessel, passageway, orifice or cavity of the body. For specific applications, the anchoring member or balloon may be specifically configured such that, when inflated, such anchoring member or balloon will conform to the shape of a specific anatomical structure. Further, it is preferable that such inflatable anchoring member or balloon, when in its deflated state, be sufficiently elastic and specifically constructed to fully retract against or within a portion of the guidewire body such that the deflated balloon does not extend or protrude outwardly beyond the outer-most surface of the portions of the guidewire body adjacent said anchoring member or balloon.

The check valve component of the present invention may comprise any suitable type of valving apparatus or valving mechanism capable of carrying out a one-way valving function to prevent deflation of the inflatable anchoring member or balloon until such time as a human operator volitionally deactuated the check valve to permit deflation of said anchoring member/balloon.

Further aspects and objects of the invention may become apparent to those skilled in the art upon reading and understanding the following detailed description and the accompanying drawings.

DETAILED DESCRIPTION OF THE PREFERRED EMBODIMENT

The following detailed description and the accompanying drawings are provided for purposes of describing and illustrating presently preferred embodiments or examples of specific embodiments of the invention only. This description and accompanying drawings are not intended to limit the scope of the invention in any way.

i. Overall Configuration and Operation of an Anchorable Guidewire

The anchorable guidewire device 10 shown in the accompanying drawings generally comprises (a) an elongate guidewire body 12; (b) an inflatable anchoring member or balloon 14 disposed or mounted on the guidewire body 12; (c) a fluid injection port formed in the open proximal end of the guidewire body; (d) a hollow lumen 26 extending from the open proximal end of the guidewire body to the distal end cap 35 thereof; (e) an aperture 28 to allow passage of fluid between the hollow lumen 26 and the interior 30 of the inflatable balloon; and (f) a check valve apparatus 16 positioned on the open proximal end (P) of the guidewire body 12 to prevent inadvertent or uncontrolled deflation of the balloon 14.

The check valve 16, a preferred embodiment of which is hereinafter described more fully, is preferably smaller in outer diameter or maximum outer dimension than the inner diameter of any catheter, scope or other instrument to be passed thereover. To wit, in applications wherein tubular scope(s), catheter(s) or other instrument(s) of known inner diameter are to be withdrawn/advanced over the guidewire 10, the outer diameter or largest outer dimension of the check valve 16 will be smaller than the known inner diameter or smallest inner dimension of such catheter(s), scope(s) or instrument(s) to be passed thereover so as not to interfere with or cause damage to such catheter(s), scope(s) or instrument(s).

To facilitate injection of inflation fluid into the balloon 14, a removable connector, Luer adaptor or hub 18 may be mounted on the body of the check valve 16 and/or elsewhere on the guidewire body 12. Such removable hub 18 is configured to receive a syringe 20 in fluid connection thereto such that the syringe may be used to inject balloon inflation fluid through the check valve 16, through the open proximal end of the guidewire body 12, and through the lumen 26 for the purpose of inflating the balloon 14, when needed.

Figure 3:
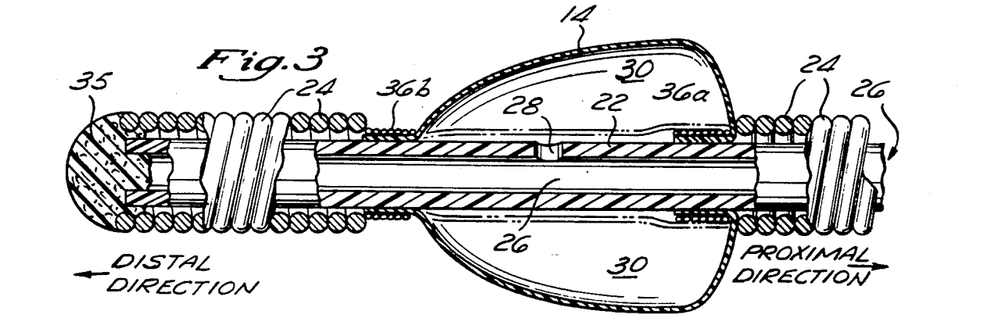
FIG. 3 is a longitudinal sectional view of the distal end portion of a presently preferred embodiment of the invention.

In many embodiments, it will be desirable for the distal end or distal tip of the guidewire device 10 to comprise a blunt, rounded, closed distal tip (e.g. FIG. 3). Also, the distal tip or distal-most portion of the guidewire may be constructed so as to be more flexible than the remainder of the guidewire body 12 so as to avoid trauma to anatomical structures as the guidewire is inserted and advanced.

The device 10 may optionally incorporate one or more additional infusion/withdrawal lumens running through the guidewire of the body. Such additional lumen(s) may open through one or more ports or apertures formed in the distal tip of the catheter body 12 or elsewhere thereon to provide the capability of infusing-/aspirating various perfusion solutions, medicaments or other fluids through such optional additional lumen(s) irrespective of whether the anchoring or balloon is in its inflated or deflated state.

ii. A Preferred Construction of the Guidewire Body

In the embodiment shown, inflation of the balloon is effected by mounting a detachable Luer adaptor or hub 18 on the outer body of check valve 16. A syringe 20 is operatively connected to the detachable hub 18 and, thereafter, the syringe 20 is used to inject a desired amount of balloon inflation fluid through the check valve 16, lumen 26, aperture 28 and into the interior 30 of the balloon 14, thereby causing inflation of the balloon 14. After the balloon has been fully inflated, the check valve 16 will prevent proximally directed backflow of balloon inflation fluid, thereby maintaining the then-present fluid pressure within the balloon interior 30 and lumen 26 and allowing the syringe 20 and hub 18 to be detached without resultant fluid backflow and deflation of the balloon 14. After the syringe 20 and detachable hub 18 have been removed, a tubular catheter, scope or other instrument of relatively small diameter may be advanced and/or retracted over the outer surfaces of the guidewire body 12 and check valve 16, with the anchoring balloon 14 remaining fully inflated so as to firmly anchor the distal end of the guidewire during such procedure. When it is desired to deflate the balloon 14, the operator may manually open or deactuate the check valve 16 by applying distally directed pressure to the depressible needle 32. Such opening or deactuation of the check valve 16 will permit the balloon inflation fluid to flow out of the proximal opening 38 of the check valve 16, thereby allowing the balloon 14 to deflate to its fully deflated configuration as denoted by the phantom lines on FIG. 3.

Figure 8:
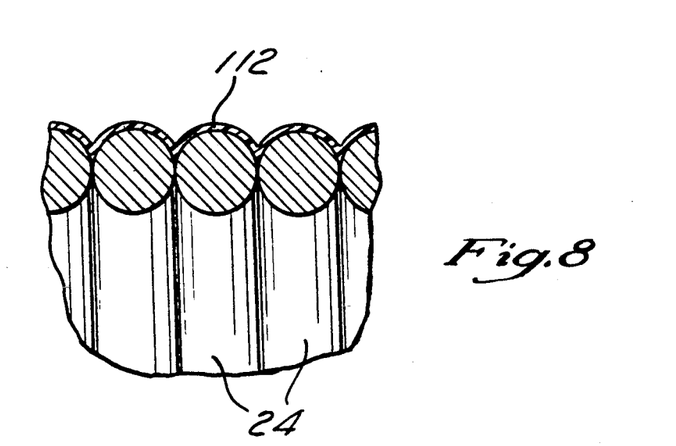
FIG. 8 is a cut-a-way perspective view of a portion of an anchorable guidewire the present invention having a fluid tight coating 112 formed on the outer surface thereof.
Figure 9:
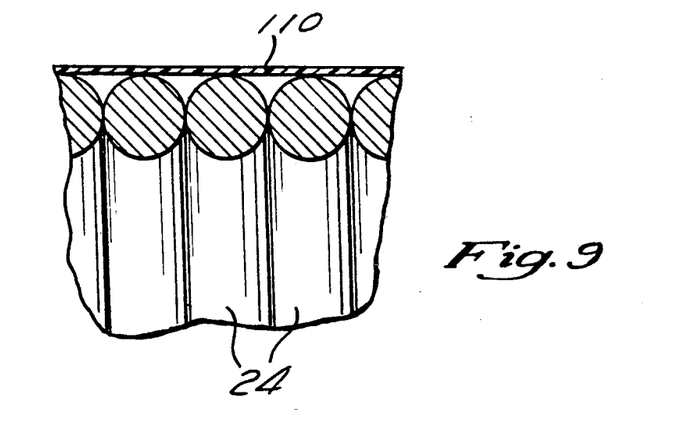
FIG. 9 is a cut-a-way perspective view of a portion of an anchorable guidewire the present invention having a fluid tight outer tubular member disposed on the outer surface thereof.

It will be appreciated that, as an alternative to a hollow balloon inflation lumen extending through the body of the guidewire, any other suitable tube, channel fluid passageway or other fluidic connection may be formed on the outer surface of, or adjacent to the guidewire body to facilitate flow of balloon inflation fluid from an injection or introduction port which resides outside of the patient's body, into the interior compartment 30 of the balloon 14. In embodiments, such as those shown in FIGS. 8 and 9 where an outer tubular member 110 or continuous outer coating 112 are disposed on the outer surface of a coiled wire type guidewire body, it may be unnecessary to incorporate or utilize an inner tubular member within the lumen of the wire coil as the outer tubular member 110 or coating 112 will form an adequate fluid tight closure around such wire coil 24.

Referring to the detailed showing of FIG. 3, a preferred embodiment of the present invention generally incorporates a guidewire body 16 formed of an inner tube member 22 having a wire coil 24 disposed therearound. The inner tube member 22 may be formed of any material which exhibits the physical properties and/or other properties (e.g. biocompatibility) required for performance of the intended application. In many guidewires of the embodiments of the invention intended for use in gastroenterologic, urological or cardiovascular procedures, the guidewire will be sufficiently flexible to be advanced through tortuous or curved passageways or ducts of the body. In such embodiments the inner tube 22 may preferably be formed of stainless steel hypodermic tubing. Alternatively, the inner tube may be formed of polyurethane or other types of flexible biocompatible plastic medical tubing.

The inner tube member 22 has an elongate hollow lumen 26 which extends at least partially therethrough. It is preferable that such lumen 26 have a proximal opening through the proximal end P of the guidewire body 12, so as to fluidly communicate with the interior or inner passageway of an attendant check valve 16 mounted thereon. It is further preferable that the hollow lumen 26 extend from the proximal end P of the guidewire body 12 to a point at least adjacent to a balloon inflation/deflation aperture 28 so that a balloon inflation gas or liquid (e.g. a radiopaque inflation fluid) may be injected in a distal direction through the check valve 16, lumen 26 of the inner tube 22, out of the balloon inflation/deflation aperture 28 and into the interior 30 of balloon 14, thereby effecting inflation of the balloon 14. Also, by such construction, when it is desired to deflate the balloon 14, the balloon inflation fluid may be expelled from the interior 30 of the balloon 14, inwardly, through the balloon inflation/deflation aperture 28, through lumen 26, and out of the proximal end of the device 10.

In the embodiment shown in FIG. 3, a blunt distal tip plug 35 is positioned on the distal end of the guidewire body 12 so as to form a smooth, blunt, closed distal tip. It will be appreciated that, in many embodiments of the invention, one or more separate and additional fluid lumens (not shown) may extend through the guidewire body 12 and may open through one or more openings or ports located in the distal tip and/or sidewalls of the guidewire body 12 so as to permit infusion of oxygenated perfusion solutions, radiographic contrast solutions, medicaments or other fluids through the guidewire body, past the inflatable balloon 14.

In the presently preferred embodiment shown in FIG. 3, the outer diameter of the guidewire body 12 is preferably approximately 0.028-0.038 inches. The wire coil 24 of the guidewire body 12 is preferably formed of stainless steel wire having a diameter of approximately 0.004-0.008 inches and formed in a coil having an outer diameter of approximately 0.021-0.038 inches. The inner tube member 22 of the presently preferred embodiment has an outer diameter of approximately 0.010-0.018 inches and an inner diameter of approximately 0.003-0.008 inches.

Generally, guidewires of the present invention will be formed in sizes and lengths which are the same as those of standard guidewires of the prior art.

iii. A Preferred Construction Mounting and Operation of the Check Valve

Figure 4:
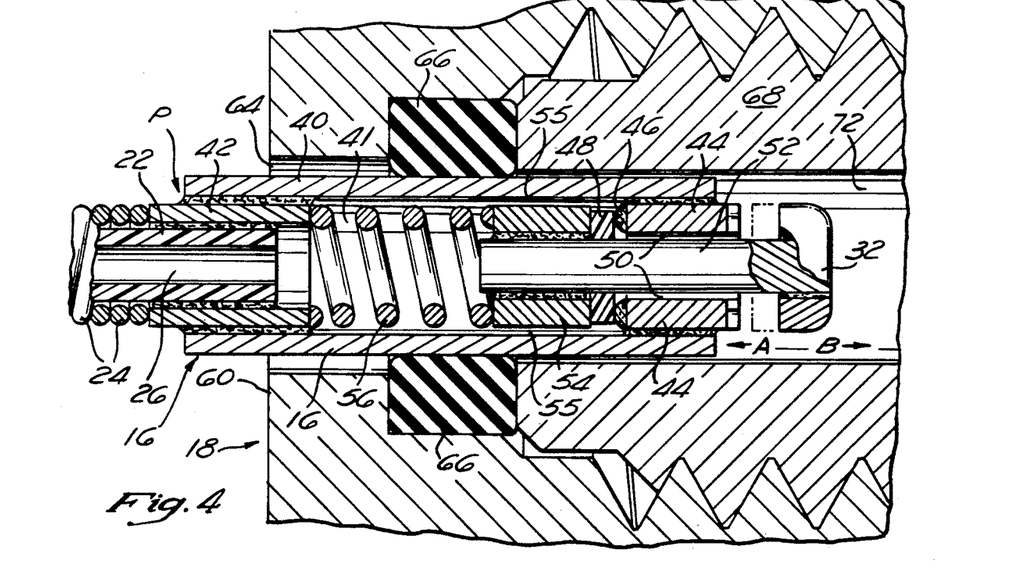
FIG. 4 is a longitudinal sectional view of the check valve portion of a preferred embodiment of the present invention having a removable proximal Luer hub operatively mounted thereon.

In the particular embodiment shown in FIG. 4, the check valve 16 comprises an outer tubular sleeve 40 formed of any suitable tubular material such as rigid stainless steel hypodermic needle tubing. It is preferable that the outer diameter of the outer tubular sleeve 40 be approximately the same as or only slightly greater than the outer diameter of the guidewire body 12. In most applications, the outer diameter of the guidewire body 12 will be within the range of approximately 0.028-0.038 inches and, accordingly, it is preferable that the diameter of the outer sleeve member 40 of the check valve 16 be no greater than the diameter of the particular guidewire body incorporated in that device 10.

In the preferred embodiment shown in FIG. 3, the guidewire body 12 has an outer diameter of 0.89 mm or 0.03 inches and the outer tubular sleeve 40 of the check valve 16 has an outer diameter of 0.0355 inches and an inner diameter of 0.305 inches.

A distal sleeve member 42 is inserted into the distal end of the lumen of the outer tubular sleeve 40 as shown. The distal sleeve member is bonded or attached to the luminal surface of the outer sleeve member 40 by way of weldments, braze, solder or adhesive.

A portion of the inner tube 22 immediately adjacent the proximal end thereof is preferably devoid or denuded of surrounding wire coil 24 so as to be insertable directly into the lumen of the distal sleeve member 42, as shown. When so inserted, the proximal end of the inner tube member 22 is then bonded or affixed to the inner luminal surface of the distal sleeve member 42 by way of weldments or adhesive. Such firmly affixes the guidewire body 12 to the check valve 16.

A proximal sleeve member 44 is inserted into the proximal end of the lumen of the outer tubular sleeve 40, as shown. The proximal sleeve member 44 is affixed to the luminal surface of the surrounding outer tubular sleeve 40 by weldments, braze, solder or adhesive.

A valve seat 46, comprising a raised ridge of epoxy or other rigid material may be disposed on the distal surface or distal face of the proximal sleeve member 44 such that seal 48 will firmly seat thereagainst to form substantially fluid tight contact therebetween.

A needle valve member 32 extends fully through the lumen of proximal sleeve member 44. The shaft portion 52 of the needle valve member 32 is slightly smaller in outer diameter than the inner diameter of the lumen of the proximal sleeve member 44 so as to allow for passage of balloon inflation fluid through space 50 between the outer surface of the shaft portion 52 of the needle valve member 32 and the inner luminal surface of the proximal sleeve member 44. By such arrangement, the shaft 52 of needle valve member 32 remains movable back and forth (proximally and distally) within the lumen of the proximal sleeve member 44.

A cylindrical plunger component 54 is affixed to shaft by weldments, braze, solder or adhesive. Such plunger component 54 may be formed of a segment of steel needle or hypodermic tubing of the same size and type used to form the proximal sleeve member 44 and distal sleeve member 42. As shown, it is preferable that the distal end of the shaft 52 extend slightly beyond the distal-most edge of the plunger component 54 to facilitate seating within spring 56, as described more fully herebelow.

A cylindrical elastomeric seal 48 is positioned around shaft 52 and/or in abutment with the proximal edge of plunger component 54. Such elastomeric seal 48 may be bonded to the outer surface of shaft 52 and/or to the proximal surface of the plunger component 54, by way of an adhesive material or mechanical interference. The elastomeric seal 48 may be formed of any suitable material(s) capable of functioning to form an essentially fluid tight seal against the opposing seat 46.

In the preferred embodiment shown, the elastomeric seal 48 comprises a segment of silicone tubing (SILASTIC ™ Tubing, Dow Corning Corporation, Midland, Mich.). Such seal 48 is preferably approximately 0.025 inches in length and preferably has an unstressed inner diameter of 0.012 inches and an outer diameter of 0.025 inches.

A spring member 56 is disposed between the distal face of the plunger component 54 and the proximal face of the distal sleeve member 42. Such spring member 56 preferably comprises a thin wire coil such as 0.007 inches diameter stainless steel having an outer diameter which is approximately equal to, or slightly smaller than, the inner luminal diameter of the outer sleeve member 40. The length of the spring member 56 is preferably slightly greater than the distance from the distal face of the plunger component 54 to the proximal face of the distal sleeve member 42 so that the spring member 56 will exert sufficient continual pressure to hold the elastomeric seal 48 in fluid tight sealing contact with the opposing seat 46 formed on the distal face of proximal sleeve member 44. However, the tension exerted by spring 56 is sufficiently low to permit the needle valve body 32 to be depressed in the direction of arrow A by air pressure exerted by syringe 20 or by manual finger pressure exerted by the human operator.

In the embodiment shown in FIG. 4, the distance between the proximal face of distal sleeve member 42 and the distal face of plunger 54, when needle valve 32 is in its full proximally retracted "closed" position, as shown, is 0.20 inches. Also, the unstressed length of the preferred spring 56 is 0.22 inches. Thus, even when the needle member 32 is in its fully closed proximally retracted position, the spring member 56 is slightly compressed so as to maintain exertion of pressure in a proximal direction on plunger 54, thereby maintaining a fluid tight seal between seal 48 and seat 46.

By such arrangement, syringe 20, mounted on detachable hub 18, may be utilized to inject fluid at a sufficient pressure, such as 10–20 psi opening pressure, to cause depression of the needle valve member 32 in the direction of arrow A, thereby causing the elastomeric seal 48 to move away from the opposing seat 46 and, thus, allowing fluid to pass through space 50 between the parted seal 48 and seat 46, through space 55, through inner bore 41, and through lumen 26 to effect inflation of the balloon. After the balloon has been fully inflated, the pressure within lumen 26 will be greater than ambient, and such positive pressure will cause the needle valve member 32 to maintain fluid tight sealing contact between seal 48 and seat 46, thereby preventing backflow of fluid out of the check valve 16. Under such conditions, the syringe 20 and surrounding detachable hub 18 may be fully removed from the check valve 16 without resultant deflation of the balloon 14 until such time as a human operator exerts distally directed manual pressure against needle valve member 32 in the direction of arrow A, compressing spring 56 and causing seal 48 to part from seat 46, thereby allowing the pressure within the lumen 26 and interior of the check valve 16 to equalize with ambient pressure such that the elastic balloon 14 may become fully deflated.

As an alternative to the valving apparatus described above, various other types of valving apparatus or valving mechanisms may be mounted within the check valve body, or within the lumen of the guidewire body 16, to effect the herein described check valve function. Such alternatively usable valving apparatus or valving mechanisms include all presently known or hereafter devised types of check valve mechanisms or check valve apparatus capable of performing the herein described function of the present invention. Included among the various alternative types of check valve apparatus or check valve mechanisms are (a) flexible leaflet or flap type valving apparatus, (b) ball-in-seat type valving apparatus, and (c) diaphragm type valving apparatus. One example of a flap or leaflet valving apparatus which may be used in the present invention is a simple inline valving apparatus having a plurality of pliable or flexible valve flaps mounted within the inner bore of check valve body such that the individual flaps or leaflets abut one another to prevent proximally directed backflow of fluid through the check valve. Such flap members or leaflets are, however, separable upon exertion of pressure thereon by the infusion of fluid in a distal direction and/or by being contacted directly by the tip or end of a syringe or other injection member which may be inserted between such flap members. In the present invention, the manual deactuation of such flap member/leaflet type check valve apparatus may be effected by inserting a blunt needle stub or syringe tip between the flap members/leaflets so as to separate such flap members/leaflets allowing proximally directed venting of fluid therethrough. Other types of specific valving apparatus or valving mechanisms known in the art which may be used in the present invention include various needle valves of the type utilized for inflation of pneumatic tires.

iv. Preferred Construction of the Detachable Hub

The detachable hub 18 which is mountable on the proximal end of the guidewire device 10 may comprise any suitable type of detachable hub capable of firmly mounting on the guidewire to effect attachment of an attendant syringe 20 thereto such that fluid may be injected by the syringe to depress the needle member 32 of check valve 16 and to thereby infuse fluid through the inner lumen 26 of the guidewire assembly 10 to inflate the inflatable anchoring member or balloon 14 thereof. An example of a commercially available detachable hub which may be usable with some or all embodiments and/or sizes of the present invention is PFLLA-UCC, Cook Inc., Bloomington, Ind.

Figure 1:
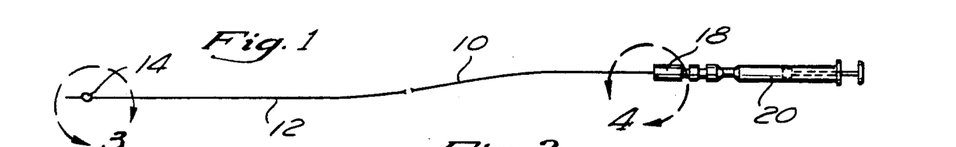
FIG. 1 is a side elevational view of a balloon anchorable guidewire device of the present invention having a detachable proximal hub and hypodermic syringe attached thereto.
Figure 2:
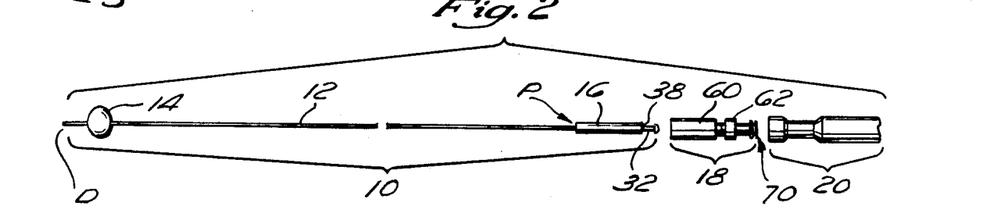
FIG. 2 is an exploded elevational view of a balloon anchorable guidewire device of the present invention having a detachable proximal hub and hypodermic syringe positioned relative thereto.

One embodiment of a usable, detachable hub member 18 is shown in FIGS. 2 and 4. As shown, this embodiment of the detachable hub 18 comprises a distal body member 60 and a proximal body member 62. The distal body member 60 comprises a generally cylindrical rigid body formed of molded plastic or other suitable material. A hollow inner bore 64 extends fully through the distal body 60. A compressible elastomeric sealing ring 66 is mounted within the inner bore 64 of the distal body 60. The proximal portion of the inner bore 64 is threaded interiorly to form a female receiving receptacle immediately adjacent to the elastomeric sealing ring 66. The male portion 68 of the proximal member 62 comprises a male threaded member which may be rotatably advanced into the female receptacle portion of the distal member 60 such that the distal tip of the proximal member 62 abuts against and compresses the compressible elastomeric sealing ring 66. Such compression of the elastomeric sealing ring 66 causes the elastomeric sealing member to flow inwardly and to compress against the outer walls of the outer sleeve member 40 of check valve 16, thereby firmly mounting the detachable hub 18 on the body of the check valve 16. Thereafter, an attendant syringe 20 or fluid administration tube may be connected to the receiving end 70 of the detachable hub 18. Fluid injected by the syringe 20 or attendant infusion tube will then flow through the inner bore 72 of the proximal portion 62 of the hub member 18 and into the space 50 around the shaft portion 52 of the needle member 32 of check valve 16. Pressure created by such fluid flow will cause the needle member 32 to advance distally in the direction of arrow A, thereby causing the seal 48 to part from seat 46 and allowing fluid to flow through the space 55 and bore 41 of the check valve and subsequently into and through the inner lumen 26 of the guidewire device 10. When the positive pressure of fluid injection from the syringe 20 or attendant infusion line is ceased, the relative internal pressure of the fluid within the device 10 will cause the needle member 32 to retract in the direction of arrow B until seal 48 meets with seat 46, thereby forming a fluid tight check or seal preventing further backflow of fluid out of the distal end of the check valve 16. Thereafter, the proximal member 62 may be retracted or unscrewed from the distal body member 60 sufficiently to relieve pressure on the elastomeric sealing ring 66 such that the elastomeric sealing ring 66 will assume its original configuration and will no longer abut against the outer sleeve member 40 of the check valve 16. Such will release the detachable hub 18 from the body of the check valve 16 such that the detachable hub 18 and any attendant syringe 20 may be fully removed and discarded, thereby leaving only the relatively small diameter check valve 16 and guidewire body 12 in place.

The compressible elastomeric sealing ring 66 of the detachable hub 18 may be formed of a cut segment of rubber such as Buna-N or silicone tubing (e.g. SPASTIC Tubing, Dow Corning, Michigan) with an unstressed ID slightly larger than the OD of the valve body. Alternatively, the sealing ring 66 may comprise an O-ring or other compressible elastomeric member or plurality of member(s) capable of flowing upon compression so as to exert pressure inwardly against the body of check valve 16.

v. Preferred Construction, Mounting and Operation of Anchoring Balloon

The inflatable anchoring member or balloon 14 may be mounted at any location on the body 12 of the guidewire, as shown in FIGS. 1, 2, 3, 5 and 6. Alternatively, as shown in FIG. 7, the balloon 14 may be mounted on the distal tip of the guidewire so as to extend outwardly or away from the distal tip (D) when inflated. The exact location at which the balloon 14 is mounted may be determined on the basis of the intended mode of use or intended application of the device 10.

In the embodiment shown in FIG. 3, the inflatable anchoring member comprises a balloon 14 of tubular configuration attached annularly about the outer surface 34 of the inner tube member 22, near the distal end of the device 10. A preferred material for forming the balloon 14 of the present invention comprises elastic latex tubing, having a wall thickness of approximately 0.001–0.005 inches and preferably about 0.003 inches. At the location where the balloon is to be mounted, a portion of the outer wire coil 24 equal in length to the length of the balloon 14 to be mounted, is eliminated or absent so as to expose the underlying outer surface 34 of the inner tube 22. One end of the elastic tube used to form the balloon 14 is initially disposed about the proximal most region of the exposed portion of the inner tube 22 and is firmly affixed thereto by wrapping or tying a thread or suture material 36a therearound. The latex tube is then folded over itself, in a distal direction as shown, and the opposite end of the balloon 14 is attached to the distal-most portion of the exposed portion of the inner tube 22 by wrapping or tying of thread or suture material 36b therearound.

It is preferable that the outer diameter of the balloon 14, when in its fully deflated and unstretched state, be approximately the same as, or smaller than, the outer diameter of the guidewire body 12. Also, the material of which such balloon 14 is formed is preferably sufficiently elastic such that, after the balloon 14 has been fully inflated, the balloon 14 will elastically contract or return to substantially its original diameter so as to once again fully collapse or contract against the underlying outer surface 34 of the inner tube 22 (as indicated by the phantom lines on FIG. 3) so as not to protrude or extend outwardly beyond the adjacent outer circumference X, X' or outer-most surface of the coiled wire 24 covering. To achieve this level of elasticity, it is preferable that the balloon 14 be formed of material capable of undergoing elongation of 900% ±50% at room temperature (i.e. percent elongation). One presently preferred material for forming tubular balloons is a proprietary latex material capable of undergoing elongation of 740% ±16% at room temperature (i.e. percent elongation). A second preferable material is that known as Surethane (Cardia Control Systems, Inc. Other embodiments may be successfully constructed using balloon materials which have elongation properties greater than or less than the exemplary choices cited. However, in most applications, the material selected should exhibit a minimum elongation of 100% at room temperature. It is further preferable that the balloon 14 be sized, constructed and configured such that, when it is completely deflated, it will assume a single thickness, flat configuration without infolding, invagination, pleating, puckering or the formation of slackened or folded areas within the body of the deflated balloon.

In certain applications, such as cardiovascular applications wherein the balloon is to be inflated within an artery or vein, it may be desirable to form the balloon such that, when fully inflated, there will exist one or more longitudinal grooves, invaginations, flow-through channels or other openings extending through the body of the balloon 14 to allow blood to flow past the balloon even when the balloon is fully inflated and in contact with the surrounding blood vessel wall. Such longitudinal grooves, invaginations, flow-through channels or other openings will be sized to allow some flow of perfusing blood past the balloon 14 while, at the same time, leaving enough of the balloon 14 in contact with the surrounding blood vessel wall to hold or anchor the guidewire in place relating to such blood vessel wall.

vi. Operation and Use of the Anchorable Guidewire

The anchorable guidewire device 10 of the present invention may be used in numerous clinical applications wherein it is occasionally desirable to anchor a guidewire in place for a period of time after insertion thereof. Clinical procedures wherein the anchorable guidewire 10 may be employed include, but are not limited to, wire-guided dilatations of gastrointestinal strictures, endoscopic retrograde cholangiopanoreatography, wire-guided dilation of urinary tract strictures or blockages, procedures for retrieving stones (e.g. gallstones, kidney stones, bladder stones), percutaneous transhepatic cholangiography, laparoscopic explorations of the common bile duct or other intra-abdominal anatomical structures, transcervical retrograde fallopian tube cannulation, other gynecological procedures, and various cardiovascular procedures such as angioplasty, angiography and valvuloplasty procedures.

Figures 5, 6, 7:
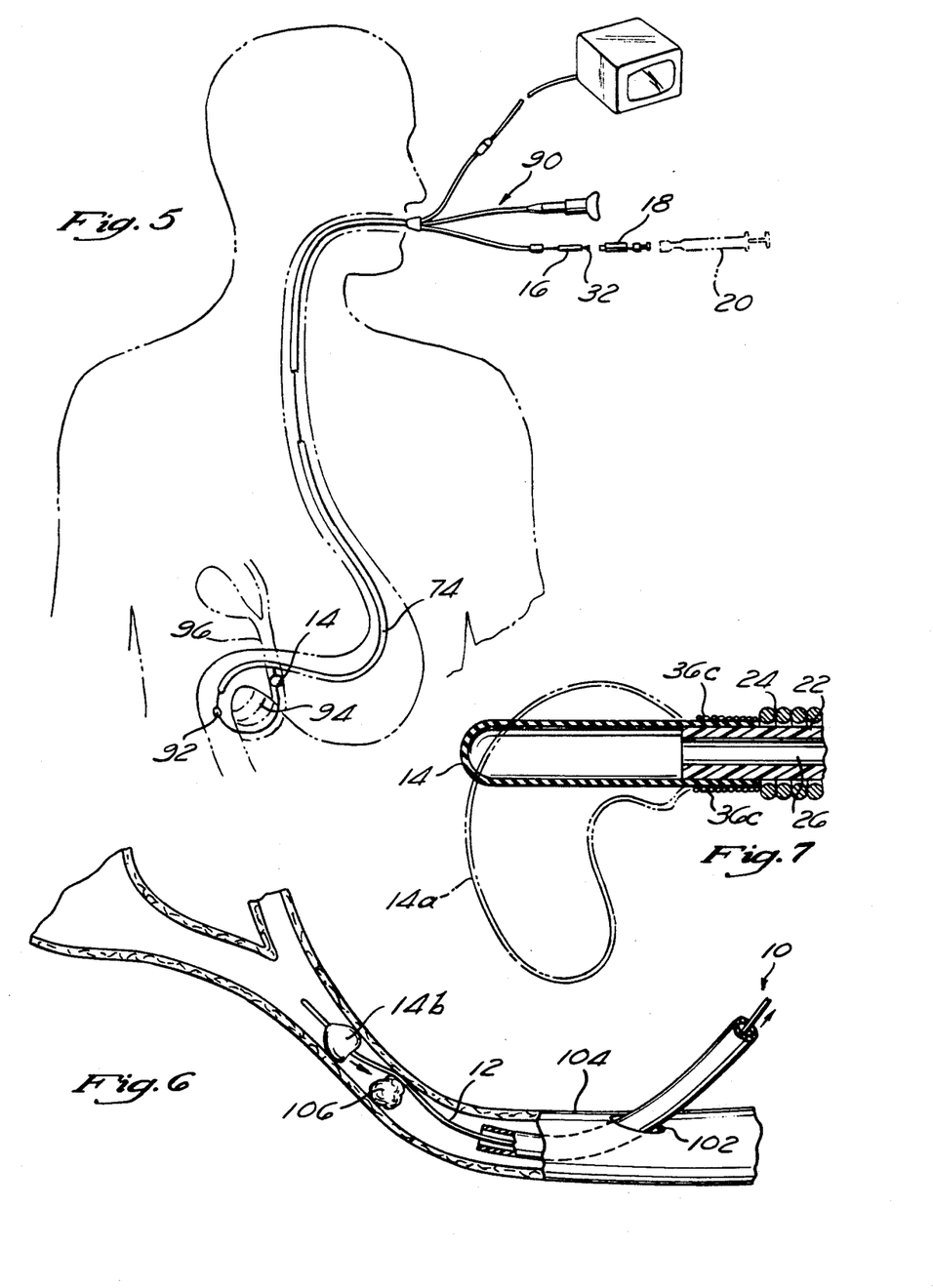
FIG. 5 is a schematic diagram of an application of the invention wherein an anchorable guidewire of the present invention has been inserted transesophogeally and advanced through a portion of the biliary tree, to a position where the distal tip of the guidewire is located within the pancreatic duct.
FIG. 6 is a schematic diagram of an application of the invention wherein an anchorable guidewire of the present invention has been inserted into the common bile duct, through a laparoscopically placed catheter, and advanced past a singular gallstone located within the common bile duct.
FIG. 7 is a longitudinal sectional view of the distal end of an anchorable guidewire of the present invention incorporating an inflatable anchoring balloon which, when inflated, assumes a laterally hooked or bent configuration.

FIG. 5 illustrates one example of a use of the anchorable guidewire 10 of the present invention in a procedure known as endoscopic retrograde cholangiopancreatography (ERCP).

In general, the ERCP procedure comprises initially inserting a duodenoscope 90 transesophogeally and advancing the distal end of the scope 90 through the pylorus and into the duodenum. The duodenoscope is then utilized to visually locate an anatomical opening known as the ampulla of Vater 92. Both the pancreatic duct 94 and common bile duct 96 may be accessed through the ampulla 92. An anchorable guidewire 10 of the present invention is then advanced through the duodenoscope 90 until the distal end of the guidewire 10 emerges out of and extends beyond the distal end of the scope 90. Under direct endoscopic visualization, the distal end of the guidewire 10 is then inserted into the ampulla 92 and initially advanced into the pancreatic duct 94. With the guidewire 10 positioned in the pancreatic duct, a small catheter (not shown) may subsequently be advanced over the guidewire 10 and into the pancreatic duct where such catheter may be used to inject radiopaque dye for the purpose of diagnostic imaging of the pancreatic duct 94. Thereafter, the catheter (not shown) and guidewire 10 are retracted from the pancreatic duct 94 and inserted into the common bile duct 96 wherein the dye infusion procedure is once again carried out for the purpose of diagnostic imaging of the common bile duct. The guidewire 10 may then be reinserted into the pancreatic duct to guide the placement of an instrument or catheter for collecting pancreatic secretions for cytological interpretation and analysis.

During the ERCP procedure, it may be desirable to occasionally or periodically anchor or hold the guidewire in a fixed position within the pancreatic duct 94 or common bile duct 96 for a period of time while the catheter (not shown) or scope 90 is advanced, retracted, manipulated or exchanged. To effect such anchoring of the guidewire 10 the balloon 14 is inflated to a diameter whereat the balloon will engage and exert pressure against the surrounding walls of the duct (94 or 96) in which the guidewire 10 is positioned. The pressure exerted by the balloon 14 is sufficient to hold the distal end of the guidewire within such duct (94 or 96) and to prevent inadvertent extraction or dislodgment of the guidewire.

Inflation of the balloon 14 is effected by mounting the detachable hub 18 on the body of the check valve 16 at the proximal end of the guidewire device 10. The detachable hub 18 is mounted on the body of check valve 16 by initially inserting approximately half of the proximal end of the check valve 16 into the distal end of the inner bore 64 of the distal body portion 60 of the detachable hub 18. The proximal body member 62 of the detachable hub 18 is then threaded and inserted into the proximal end of the distal hub portion 60, causing compression of the elastomeric sealing ring 66 such that elastomeric sealing ring 66 will abut against the outer surface of the check valve 16, thereby forming a fluid tight seal therebetween and holding the detachable hub member 18 in place of the proximal end of the check valve 16.

A syringe 20 is then mounted on the detachable hub 18 and utilized to inject sufficient gas or other fluid through the lumen of the guidewire 10 to cause inflation of balloon 14. Thereafter, the syringe 20 and detachable mounting hub 18 may be removed from the guidewire device 10. The preferred detachable hub 18 is removed from the body of the check valve 16 by unscrewing and removing the proximal body portion 62 from the distal body member 60, thereby decompressing the elastomeric sealing ring 66. Such decompression of the elastomeric sealing ring 66 allows the elastomeric sealing ring 66 to return to its original configuration, thereby releasing the detachable hub 18 from the body of the check valve 16.

Upon removal of the syringe 20 and detachable mounting hub 18 the check valve 16 will operate to prevent backflow of fluid and deflation of balloon 14. Also, after the syringe 20 and detachable mounting hub 18 have been removed an attendant catheter may be advanced or retracted over the body of the relatively small diameter check valve 16 and advanced over the guidewire body 10 as desired. Additionally, the duodenoscope 90 could be extracted and/or reinserted over the relatively small diameter check valve 16.

When it is desired to deflate the balloon 14 to allow extraction of the guidewire 10, the operator may simply depress the needle portion 32 of the check valve 16, thereby causing the check valve 16 to open or otherwise deactuate to allow backflow of fluid and deflation of balloon 14. Thereafter, the entire guidewire device 10 may be easily extracted from the body along with the attendant duodenoscope 90, catheter (not shown) and/or any other type of instrument which may have previously been advanced over the guidewire body 12.

The above-described application of the present invention in ERCP procedures is but one example of many possible clinical applications of the anchorable guidewire device 10 of the present invention. It will be appreciated that the anchoring member or balloon 14 may be specifically sized, positioned and configured to fit and function within any type of anatomical structure into which the guidewire may be inserted including blood vessels, ducts, vesicals (e.g. gallbladder, urinary bladder) and cavities of the body.

In addition to performing an anchoring or holding function, the inflatable anchoring member or balloon 14 may also be utilized to accomplish various utilitarian functions. For example, in certain applications, the balloon 14 may be used to stretch or dilation of a surrounding anatomical structure or to dislodge, pull or otherwise remove a foreign object or calculus which has become lodged within a duct or passageway of the body. One example of such utilitarian use of the anchoring member or balloon 14 is shown in FIG. 6. FIG. 6 illustrates an application wherein, prior to performance of a laparoscopic cholecystectomy, a catheter 100 has been inserted transabdominally and advanced through a small incision 102 in the distal portion of the common bile duct 104. Such catheter 100 is initially used to inject radiopaque dye into the common bile duct 104 to ascertain the patency thereof. If such radiologic visualization of the common bile duct 104 reveals, as shown in FIG. 6, the presence of a gallstone 106 lodged within the common bile duct 104, it becomes desirable to remove such gallstone 106 *prior* to performing the cholecystectomy procedure. Indeed, the presence of an occluding gallstone 106 within the common bile duct is considered to be a contraindication to the use of the laparoscopic technique for removal of the gallbladder. Because the inflatable anchoring member or balloon 14b of the present invention is specifically constructed to assume, when deflated, a flat, compact profile which does not extend outwardly beyond the adjacent outer-most surface of the guidewire body 16, the presence of such deflated balloon 14 will not interfere with passage of the guidewire device 10 through the lumen of the previously inserted catheter 100, and through the common bile duct to a point where the balloon has been advanced past the lodged gallstone 106. Thus, the guidewire may be so inserted and the balloon 14b may then be inflated in a position between the gallbladder and the lodged stone. Thereafter, the guidewire body 12 may be retracted in the direction of arrow X so as to pull or move the gallstone 106 toward the incision 102. After the gallstone 106 has been moved to a position adjacent incision 102, the surgeon may utilize other instruments (forceps) to crush and remove the gallstone 106, thereby restoring the patency of the common bile duct 104 so that the laparoscopic cholecysteotomy procedure may continue.

To facilitate such utilitarian function of the device 10, the inflatable member or balloon 14b may be specifically configured to effect such utilitarian application. As shown in FIG. 6, for the illustrated gallstone removal application, the balloon 14b, when inflated, assumes a heart-shaped or roughly triangular configuration whereby the proximal end of the balloon 14b is of greater diameter than the distal end thereof. Such configuration may enable the balloon 14b to more easily cup, grip and push the lodged gallstone 106 through the lumen of the common bile duct 104, as desired. It will be appreciated that many other specific configurations of the balloon 14, 14a, 14b may be provided so as to render the balloon 14, 14a, 14b particularly suitable for specifically intended anchoring and/or utilitarian applications.

The invention has been described herein with specific reference to certain preferred embodiments of the invention and certain specific applications thereof. It will be appreciated that various additions, modifications, deletions and alterations may be made to the embodiments of the invention described herein without departing from the spirit and scope of the invention. Furthermore, it will be appreciated that various additional anchoring and/or utilitarian applications of the invention may be foreseeable in view of the present technology or may hereafter become feasible due to further developments in the applicable technology. It is intended that all such additional embodiments and additional applications of the invention be included within the scope of this patent application and construed as being within the scope of the following claims.

What is claimed is:

1. An anchorable guidewire comprising:
   an elongate guidewire body having a proximal end, a distal end, and an outer surface, said guidewire body comprising;
   a) an elongate inner tubular member having at least one hollow lumen extending longitudinally therethrough and an outer surface; and
   b) a coiled wire member coiled about the outer surface of said inner tube member; and
   c) said coiled wire member being absent from a first region of the outer surface of said inner tubular member so as to expose the outer surface of the inner tubular member within said first region,
   an inflatable anchoring member positioned at a first location on said guidewire body, said inflatable anchoring member being mounted on the outer surface of said innertube member within said first region;
   a fluid injection port positioned at a second location proximal to said first location; a fluidic interconnection between said fluid injection port and said inflatable anchoring member such that fluid may be injected through said injection port to cause inflation of said anchoring member;
   a deactuatable check valve apparatus to prevent deflation of said inflatable anchoring member until such time as said check valve apparatus is volitionally deactuated by a human operator to allow deflation of said inflatable anchoring member.

2. The anchorable guidewire of claim 1 wherein said elongate guidewire body comprises:
   a coiled wire member about an elongate longitudinal axis so as to devise a cylindrical guidewire body having an outer surface and a hollow lumen extending axially therethrough.

3. The anchorable guidewire of claim 2 wherein said elongate guidewire body further comprises:
   a plastic coating disposed on said coiled wire member.

4. The anchorable guidewire of claim 2 wherein said elongate guidewire body further comprises:
   a flexible tubular member disposed around the outer surface of said coiled wire member.

5. The anchorable guidewire of claim 2 wherein said coiled wire member has an outer diameter of approximately 0.021–0.038 inches.

6. The anchorable guidewire of claim 2 wherein said coiled wire member has an inner diameter of approximately 0.014–0.028 inches.

7. The anchorable guidewire of claim 2 wherein said injection port comprises an opening in the proximal end of said guidewire and wherein said "fluidic interconnection" comprises (a) a hollow lumen which extends from the open proximal end of the guidewire, at least partially therethrough and (b) an aperture in said guidewire body at said first location to permit fluid to pass into said balloon from said lumen and out of said balloon into said lumen.

8. The anchorable guidewire of claim 2 further comprising a flexible outer tube substantially surrounding said coiled wire member.

9. The anchorable guidewire of claim 1 wherein said elongate guidewire body further comprises:
   a plastic coating disposed on said coiled wire member.

10. The anchorable guidewire of claim 1 wherein said elongate guidewire body further comprises:
    a flexible tubular member disposed around the outer surface of said coiled wire member.

11. The anchorable guidewire of claim 1 wherein the inner tubular member is at least partially formed of plastic tubing.

12. The anchorable guidewire of claim 1 wherein the inner tubular member is at least partially formed of metal tubing.

13. The anchorable guidewire of claim 1 wherein said inner tubular member is at least partially formed of steel hypodermic needle tubing.

14. The anchorable guidewire of claim 1 wherein said inner tubular member has an inner diameter of approximately 0.003–0.008 in. and an outer diameter of approximately 0.010–0.018 in.

15. The anchorable guidewire of claim 1, wherein said inflatable anchoring member comprises a tubular balloon disposed fully around a portion of said guidewire body and configured such that, when inflated, said balloon will form an annular body.

16. The anchorable guidewire of claim 1 wherein said inflatable anchoring member is positioned on the distal end of the guidewire body, and is biased and configured such that, when fully inflated, said inflatable anchoring member will assume a hooked shape.

17. The anchorable guidewire of claim 1 wherein said inflatable anchoring member is formed of an elastomeric material capable of undergoing an elongation of 740% ±16% at room temperature.

18. The anchorable guidewire of claim 17 wherein said material comprises that commercially available as Surethane.

19. The anchorable guidewire of claim 1 wherein said inflatable anchoring member is formed of a material capable of undergoing elongation of at least 100% at room temperature.

20. The anchorable guidewire of claim 1 wherein said balloon is formed of a material capable of undergoing elongation of 850-950% at room temperature.

21. The anchorable guidewire of claim 1 wherein said inflatable anchoring member is sized, configured and constructed such that, when fully deflated, said inflatable anchoring member assumes a single thickness, flat configuration against the outer surface of the guidewire body.

22. The anchorable guidewire of claim 1 wherein the outer surface of the guidewire body is of cylindrical configuration having a first outer diameter and wherein said inflatable anchoring member is deflatable to a deflated configuration which is no greater in diameter than said first outer diameter.

23. The anchorable guidewire of claim 1 wherein said check valve comprises an inline check valve mounted on the proximal end of the guidewire body.

24. The anchorable guidewire of claim 1 wherein said check valve is deactuatable incorporated in said check valve to allow said check valve to be manually opened when it is desired to allow deflation of said anchoring member.

25. The anchorable guidewire of claim 1 wherein said check valve comprises:
- a generally cylindrical outer shell;
- a one-way valving apparatus disposed within said outer shell, said valving apparatus being configured and constructed to allow flow of fluid therethrough in a distal direction but to prevent backflow of fluid in the proximal direction.

26. The anchorable guidewire of claim 1 wherein said check valve comprises:
- an outer tubular sleeve having a proximal end, a distal end and a hollow inner bore extending therethrough;
- a spring disposed within the inner bore of said outer tubular sleeve;
- a needle valve member inserted into the proximal end of the outer tubular sleeve and compressible against said spring;
- an elastomeric seal member mounted on said needle valve member;
- a valve seat mounted in the inner bore of said tubular outer member opposite said seal member and engageable therewith to close said check valve;
- said needle valve member being alternately disposable in:
  - a "first" position wherein seal member is in fluid tight contact with said valve seat and said check valve is closed; and
  - a "second" position wherein said elastomeric seal member is separated from said valve seat and said check valve is "open".

27. The anchorable guidewire of claim 1 wherein said fluidic interconnection comprises a hollow lumen extending longitudinally through at least a portion of said elongate guidewire body.

28. The anchorable guidewire of claim 1 wherein said fluidic interconnection comprises a tubular member mounted on the outer surface of a portion of said elongate guidewire body.

29. The anchorable guidewire of claim 1 wherein said injection port comprises the proximal end of said guidewire and wherein said fluidic interconnection comprises a hollow lumen extending through the guidewire body from the proximal end thereof to said inflatable anchoring member.

30. An anchorable guidewire comprising:
- a tubular member having an open proximal end, a closed distal end, an outer surface and a hollow lumen extending at least partially therethrough;
- an elongate wire coil coiled about the outer surface of said tubular member;
- said wire coil being absent from a first region of said inner tubular member;
- a tubular elastic balloon member affixed to the outer surface of said inner tubular member within said first region such that an inflation space exists between said balloon member and the outer surface of said inner tubular member;
- a balloon inflation aperture formed in said inner tubular member to permit fluid to pass back and forth between said hollow lumen and said inflation space;
- a deactuatable check valve mounted on the open proximal end of said inner tubular member to prevent deflation of said balloon by backflow of fluid from said hollow lumen until such time as said check valve is volitionally deactuated by a human operator to allow deflation of said balloon.

31. The anchorable guidewire of claim 30 further comprising:
- a hub member removably mountable on said guidewire device to permit injection of balloon inflation fluid through said check valve and into said balloon.

32. The anchorable guidewire of claim 30 intended for use in placing a tubular apparatus of known inner diameter, said wire coil and said check valve being smaller than the inner diameter of said tubular apparatus thereover.

33. The anchorable guidewire of claim 31 intended for use in placing a tubular apparatus of known inner diameter, said wire coil and said check valve being smaller than the inner diameter of said tubular apparatus such that, when said detachable syringe hub is removed, the tubular apparatus may be advanced over the entirety of said anchorable guidewire device, including said check valve.

* * * * *

UNITED STATES PATENT AND TRADEMARK OFFICE
CERTIFICATE OF CORRECTION

PATENT NO. : 5,167,239
DATED : 12/01/92
INVENTOR(S) : David Cohen, et al

It is certified that error appears in the above-indentified patent and that said Letters Patent is hereby corrected as shown below:

```
Column 4, Line 19, delete "deactuated" and substitute therefore
--deactuates--.
Column 8, Line 34, after the word shaft, insert the numbers 52.
Column 11, Line 18, delete "SPASTIC" and substitute therefore
--SILASTIC--.
Column 16, Line 5, between the words member and about,
insert --coiled--.
Column 17, Line 58, between the words wherein and seal, insert
the words --said elastomeric--.
```

Signed and Sealed this

Second Day of November, 1993

Attest:

BRUCE LEHMAN

Attesting Officer

Commissioner of Patents and Trademarks